United States Patent
Yabusaki

(10) Patent No.: US 12,059,489 B2
(45) Date of Patent: Aug. 13, 2024

(54) OIL-IN-WATER TYPE DERMATOLOGICAL COMPOSITION FOR EXTERNAL USE

(71) Applicant: SHISEIDO COMPANY, LTD., Tokyo (JP)

(72) Inventor: Yusuke Yabusaki, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 220 days.

(21) Appl. No.: 17/467,207

(22) Filed: Sep. 4, 2021

(65) Prior Publication Data

US 2021/0401721 A1    Dec. 30, 2021

Related U.S. Application Data

(62) Division of application No. 16/344,997, filed as application No. PCT/JP2017/038917 on Oct. 27, 2017, now abandoned.

(51) Int. Cl.

| | | |
|---|---|---|
| A01N 37/00 | (2006.01) |
| A01N 25/00 | (2006.01) |
| A01N 37/12 | (2006.01) |
| A01N 37/44 | (2006.01) |
| A61K 8/06 | (2006.01) |
| A61K 8/31 | (2006.01) |
| A61K 8/81 | (2006.01) |
| A61K 31/215 | (2006.01) |
| A61K 31/24 | (2006.01) |
| A61Q 1/02 | (2006.01) |
| A61Q 19/00 | (2006.01) |

(52) U.S. Cl.
CPC .............. *A61K 8/8111* (2013.01); *A61K 8/06* (2013.01); *A61K 8/062* (2013.01); *A61K 8/31* (2013.01); *A61K 8/81* (2013.01); *A61Q 1/02* (2013.01); *A61Q 19/00* (2013.01); *A61K 2800/48* (2013.01)

(58) Field of Classification Search
None
See application file for complete search history.

(56) References Cited

U.S. PATENT DOCUMENTS

| 6,465,402 B1 | 10/2002 | Lorant | |
| 2003/0206955 A1* | 11/2003 | Sonneville-Aubrun | A61Q 19/007 |
| | | | 424/401 |
| 2006/0110352 A1* | 5/2006 | Milbradt | A61Q 19/00 |
| | | | 424/70.15 |
| 2012/0312316 A1 | 12/2012 | Tomita et al. | |

FOREIGN PATENT DOCUMENTS

| AU | 2005282292 A1 * | 3/2007 | ............. A01N 37/02 |
| EP | 2 583 663 A1 | 4/2013 | |
| JP | 2002-522365 A | 7/2002 | |
| WO | WO-2007004200 A1 * | 1/2007 | ........... A61K 8/0237 |

OTHER PUBLICATIONS

EP 17864996.8, Extended European Search Report dated May 15, 2020, 10 pages—English.

* cited by examiner

*Primary Examiner* — Layla Soroush
(74) *Attorney, Agent, or Firm* — Andrew F. Young; NOLTE LACKENBACH SIEGEL

(57) ABSTRACT

An oil-in-water emulsion composition for skin includes 0.2 to 2.5% by mass of polyisobutene having a relative mass in a range of 30,000 to 100,000. The composition is applied to skin except for a lip.

19 Claims, 1 Drawing Sheet

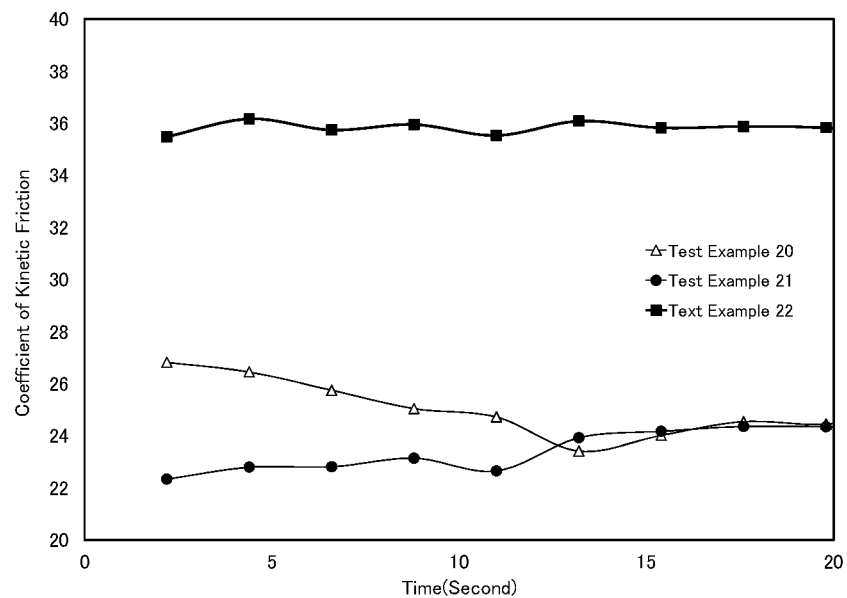

OIL-IN-WATER TYPE DERMATOLOGICAL COMPOSITION FOR EXTERNAL USE

CROSS REFERENCE TO RELATED APPLICATIONS

This application relates to and claims priority from U.S. Ser. No. 16/344,997 filed Apr. 25, 2019 the entire contents of which are incorporated herein by reference; which in turn claims priority from Ser. No.:PCT/JP2017/038917 filed Oct. 27, 2107 the entire contents of which are incorporated herein fully by reference; which in turn is based upon and claims the benefit of the priority of International Application PCT/JP2016/82362 filed on Oct. 31, 2016, the disclosure of which is incorporated herein in its entirety by reference.

FIGURE Selected for Publication

FIG. 1

TECHNICAL FIELD

The present disclosure relates to an oil-in-water emulsion composition for skin (oil-in-water external composition for skin).

BACKGROUND ART

Cosmetics including polyisobutene (polyisobutylene) are known in the art (e.g., Patent Literatures 1 to 4).

Patent Literature 1 discloses a makeup or care kit including: (i) a "combinable" composition including at least one proadhesive material selected from polyisobutylenes with relative molar masses between 150,000 and 2,200,000; and (ii) a "combined composition" including at least one diffusing compound selected from polyisobutylenes with relative molar masses which is more than 445 and less than 10,000.

Patent Literature 2 discloses an oil-in-water-type emulsion base cosmetic for lips, including polyisobutylene having a relative mass of 30,000 to 100,000, a volatile hydrocarbon oil, a pigment, a water swelling thickener, and an aqueous medium.

Patent Literature 3 discloses a sunscreen composition applicable to the human skin, the composition including, in a cosmetically acceptable medium including at least one fatty phase, at least 3% by mass of at least one oil-soluble active agent absorbing UV rays and at least one polyisobutylene which is liquid at ambient temperature and which has a viscosity-average molecular weight of between 8,000 and 65,000.

Patent Literature 4 discloses an oily makeup cosmetic, including: at least 4.5% by mass of polyisobutylene having the relative mass of 30,000 to 100,000; and a volatile hydrocarbon oil.

CITATION LIST

Patent Literature

Patent Literature 1: Japanese Patent No. 3947102B
Patent Literature 2: Japanese Unexamined Patent Publication No. 2013-35767A
Patent Literature 3: Japanese Unexamined Patent Publication No. 560-237013A
Patent Literature 4: International Publication WO2011/096337

SUMMARY OF INVENTION

Technical Problem

Polyisobutenes with relative molar masses of 150,000 or greater, as included in the makeup or care kit disclosed in Patent Literature 1, have an extremely low solubility to solvents. Thus, such polyisobutenes with high relative molar masses may be used as adhesive materials, but may be difficult to be used as a component of a cosmetic composition. On the other hand, the inclusion of polyisobutenes having relative molar masses of less than 10,000 in a cosmetic composition cannot offer the user a sufficient firm feel when the composition is applied to the skin.

The makeup base cosmetic disclosed in Patent Literature 2 is for the lips, and no consideration is given to the application of the base cosmetic to the skin other than the lips, particularly to the creation of a firm feel upon application to the skin.

The sunscreen composition disclosed in Patent Literature 3 and the oily makeup cosmetic disclosed in Patent Literature 4 are oily compositions and also include a high content by percentage of polyisobutene (polyisobutylene). Thus, application of such compositions to the skin will cause a very sticky feel to the user.

Thus, there is a demand for a composition that can provide the skin with an excellent firm feel when and/or after the user applies the composition to the skin, while suppressing stickiness.

Solution to Problem

According to a first aspect, an oil-in-water emulsion composition for skin that is applied to skin except for a lip is provided, the composition comprising 0.2 to 2.5% by mass of polyisobutene having a relative mass in a range of 30,000 to 100,000.

Advantageous Effects of Invention

When the user applies the emulsion composition for skin of the present disclosure to the skin, the user can feel excellent skin firmness. The emulsion composition for skin of the present disclosure can also suppress stickiness while achieving a firm feel.

BRIEF DESCRIPTION OF DRAWINGS

FIG. 1 is a graph showing measurement results of the coefficient of kinetic friction in Test Examples 20 to 22.

DESCRIPTION OF EMBODIMENTS

According to a preferred mode of the above first aspect, the composition further includes 0.5 to 10% by mass of a hydrocarbon oil in which the polyisobutene is soluble.

According to a preferred mode of the above first aspect, the hydrocarbon oil is volatile.

According to a preferred mode of the above first aspect, the composition further includes 0 to 3% by mass of a thickener.

According to a preferred mode of the above first aspect, the thickener includes a homopolymer and/or a copolymer including a 2-acrylamido-2-methyl sulfonic acid component or a salt thereof.

According to a preferred mode of the above first aspect, the composition further includes an elastomer.

According to a preferred mode of the above first aspect, the elastomer is 0.1 to 6% by mass.

According to a preferred mode of the above first aspect, a pigment is at most 4% by mass.

According to a preferred mode of the above first aspect, the composition is to be applied with a hand.

According to a preferred mode of the above first aspect, the composition is to be applied around an eye.

According to a preferred mode of the above first aspect, the composition is for providing a firm sensation/feel to the skin.

An oil-in-water emulsion composition for skin according to a first embodiment of the present disclosure is described below. The emulsion composition for skin of the present disclosure may include a cosmetic composition, for example.

In the following description, POE is an abbreviation of polyoxyethylene, POP is an abbreviation of polyoxypropylene, and the number in parentheses after POE or POP indicates the average number of moles of POE groups or POP groups added in the compound in question.

An oil-in-water emulsion composition for skin according to the present disclosure includes polyisobutene. Preferably, the polyisobutene has a relative mass (molecular weight) of 30,000 or greater, more preferably 40,000 or greater. If the relative mass is less than 30,000, the user cannot obtain a sufficient firm feel. Preferably, the polyisobutene has a relative mass of 150,000 or less, more preferably 100,000 or less. If the relative mass is greater than 150,000, the user will feel stickiness, and also emulsion stability will deteriorate. The term "relative mass" in the present disclosure means the viscosity average molecular weight of a polymer.

In the composition of the present disclosure, the content by percentage of the polyisobutene to the mass of the composition is preferably 0.2% by mass or greater, more preferably 0.25% by mass or greater. When the content by percentage is at least 0.2% by mass, the user will not feel stickiness and can obtain a firm feel. The content by percentage of the polyisobutene to the mass of the composition is preferably 2.5% by mass or less, more preferably 2% by mass or less. If the content by percentage is higher than 2.5% by mass, the composition will become difficult to be spread, and it will become difficult for the user to apply the composition. The user may also feel stickiness when applying the composition.

To further suppress stickiness, the content by percentage of the polyisobutene to the mass of the composition is preferably 0.4% by mass or less, more preferably 0.3% by mass or less.

The composition of the present disclosure further includes a solvent in which the polyisobutene is soluble. For example, the solvent may include a hydrocarbon oil. In order to provide a firm feel while the user is applying (rubbing in) the composition to the skin, it is preferred that the hydrocarbon oil can volatilize during application. Examples of usable hydrocarbon oils include $C_{8-16}$ volatile hydrocarbon oils. Examples of volatile hydrocarbon oils, in which polyisobutene is soluble, may include isododecane, isodecane, heptane, isohexadecane, and liquid paraffin.

In the composition of the present disclosure, the content by percentage of the hydrocarbon oil to the mass of the composition is preferably 0.5% by mass or greater, more preferably 1% by mass or greater. If the content by percentage is less than 0.5% by mass, the polyisobutene may precipitate. The content by percentage of the hydrocarbon oil to the mass of the composition is preferably 10% by mass or less, more preferably 7% by mass or less, even more preferably 5% by mass or less, further more preferably 4% by mass or less. If the content by percentage of the hydrocarbon oil is greater than 7% by mass, a large amount of oil component may remain on the skin, and the user may less likely perceive a firm feel.

Examples of commercially available products of polyisobutene may include: B10SFN (molecular weight: 40,000), B11SFN (molecular weight: 49,000), B12SFN (molecular weight: 55,000), B13SFN (molecular weight: 65,000), B14SFN (molecular weight: 73,000), and B15SFN (molecular weight: 85,000) from the OPPANOL (registered trademark) series (from BASF); Tetrax 3T (molecular weight: 25,000 to 34,900) (from JXTG Nippon Oil & Energy Corporation); and 4H (molecular weight: 40,000), 5H (molecular weight: 50,000), 5.5H (molecular weight: 53,000), and 6H (molecular weight: 60,000) from the Himol series (from JXTG Nippon Oil & Energy Corporation).

The composition of the present disclosure may further include a thickener. For the thickener, it is preferred to use, for example, an electrostatic-repulsive thickener or an associative thickener from the viewpoint of emulsion stability. For the thickener, it is possible to use the following thickeners in combination. It should be noted that, even if the thickening mechanism of any of the following thickeners is not electrostatic-repulsive or associative, such a thickener is not excluded from a thickener that may be employed herein.

Examples of the electrostatic-repulsive thickener may include taurate-based synthetic polymers and/or acrylate-based synthetic polymers. For the taurate-based polymeric thickener, it is possible to use, for example, polymers and/or copolymers (including crosslinked polymers) including 2-acrylamido-2-propane sulfonic acid (acryloyldimethyl taurine) or a salt thereof (AMPS structure) as a constitutional unit. For such thickeners, it is possible to use, for example, at least one selected from an ammonium acryloyldimethyltaurate/beheneth-25 methacrylate crosspolymer (Aristoflex (registered trademark) HMB from Clariant (Japan) K.K.), ammonium acryloyldimethyltaurate/vinylpyrrolidone copolymer (Aristoflex (registered trademark) AVC from Clariant (Japan) K.K.), ammonium acryloyldimethyltaurate/carboxyethyl acrylate crosspolymer (Aristoflex (registered trademark) TAC from Clariant (Japan) K.K.), polyacrylate crosspolymer-11 (Aristoflex (registered trademark) Velvet from Clariant (Japan) K.K.), dimethylacrylamide/sodium acryloyldimethyltaurate crosspolymer (SU-GEL from Toho Chemical Industry Co., Ltd.), hydroxyethyl acrylate/sodium acryloyldimethyltaurate copolymer (SEPINOV EMT10 PINOV from Seppic), sodium acrylate/acryloyldimethyl taurine/dimethylacrylamide crosspolymer (SEPINOV P88 from Seppic), sodium acryloyldimethyltaurate/methacrylamidolauric acid copolymer (AMO-51 from Daitoh Chemical Co., Ltd.), and acrylamide/sodium acryloyldimethyltaurate/acrylic acid copolymer (Acudyne SCP from Dow Chemical Company). For the acrylate-based synthetic polymer thickener, it is possible to use, for example, acrylate/steareth-20 methacrylate copolymer (Aculyn (registered trademark) 22 from Dow Chemical Company). For the associative thickener, it is possible to use, for example, PEG-240/decyltetradeceth-20/hexamethyldiisocyanate copolymer (Adeka Nol (registered trademark) GT-700 from Adeka Corporation).

The content by percentage of the thickener to the mass of the composition is preferably 0.10% by mass or greater, more preferably 0.3% by mass or greater. If the content by percentage of the thickener is less than 0.1% by mass, stability tends to deteriorate. The content by percentage of the thickener to the mass of the composition is preferably 2% by mass or less, more preferably 1.5% by mass or less. If the content by percentage of the thickener is greater than 2% by mass, stickiness will be intensified when the composition is applied to the skin.

Particularly, by employing a 2-acrylamido-2-propane sulfonic acid-based thickener and the polyisobutene in combination, and also employing an elastomer (described below) in combination, it is possible to intensify firmness while suppressing stickiness. In this case, the content by percentage of the 2-acrylamido-2-propane sulfonic acid-based thickener to the mass of the composition is preferably 0.1% by mass or greater, more preferably 0.3% by mass or greater. The content by percentage of the 2-acrylamido-2-propane sulfonic acid-based thickener to the mass of the composition is preferably 1% by mass or less, more preferably 0.7% by mass or less.

The composition of the present disclosure may include other thickeners in amounts that do not inhibit the effects of the present disclosure. Examples of such other thickeners may include gum arabic, carrageenan, karaya gum, tragacanth gum, carob gum, quince seed (marmelo), casein, dextrin, gelatin, sodium pectate, sodium alginate, methyl cellulose, ethyl cellulose, carboxymethyl cellulose (CMC), hydroxyethyl cellulose, hydroxypropyl cellulose, polyvinyl alcohol (PVA), polyvinylmethyl ether (PVM), PVP (polyvinyl pyrrolidone), polysodium acrylate, carboxyvinyl polymer, locust bean gum, guar gum, tamarind gum, dialkyldimethylammonium sulfate cellulose, xanthan gum, aluminum magnesium silicate, bentonite, hectorite, aluminum magnesium silicate (Veegum), sodium magnesium silicate (Laponite), and silicic acid anhydride.

The composition of the present disclosure may further include an elastomer. Adding an elastomer can reduce stickiness. Further, the coexistence of the polyisobutene and the elastomer adds softness in addition to the firm feel after applying the composition to the skin, thereby achieving a better sensation. Further, it is possible to enhance the swift finish of the composition on the skin during application.

Examples of the elastomer may include silicone elastomers (organopolysiloxanes). Examples of silicone elastomers include crosslinked silicones (crosslinked organopolysiloxane) in which a silicone polymer is crosslinked three-dimensionally. The silicone elastomer may be of an emulsion type or a non-emulsion type. An emulsion-type silicone elastomer may be a silicone elastomer in which the crosslinked moiety and/or the main chain are/is modified by a hydrophilic moiety (e.g., a polyoxyalkylene group). A non-emulsion-type silicone elastomer may be a silicone elastomer that does not include such a hydrophilic moiety. Non-emulsion-type silicone elastomers are preferred from the viewpoint of obtaining the aforementioned feel upon use.

Examples of silicone elastomers may include dimethicone crosspolymer, dimethicone/vinyl dimethicone crosspolymer, dimethicone/phenyl vinyl dimethicone crosspolymer, vinyl dimethicone/lauryl dimethicone crosspolymer, lauryl polydimethyl siloxyethyl dimethicone/bis-vinyl dimethicone crosspolymer, alkyl ($C_{30-45}$) cetearyl dimethicone crosspolymer, and cetearyl dimethicone crosspolymer.

The content by percentage of the elastomer to the mass of the composition is preferably 0.1% by mass or greater, more preferably 0.2% by mass or greater, even more preferably 0.3% by mass or greater, further more preferably 0.4% by mass or greater, even more preferably 0.5% by mass or greater. Adding an elastomer can intensify firmness while suppressing stickiness. If the content by percentage of the elastomer is less than 0.1% by mass, it will be difficult to offer a soft and firm feel after applying the composition. The content by percentage of the elastomer to the mass of the composition is preferably 6% by mass or less, more preferably 5% by mass or less, even more preferably 4% by mass or less, further more preferably 3% by mass or less. If the content by percentage of the elastomer is greater than 6% by mass, conformability during application of the composition will deteriorate, and also emulsion stability will deteriorate.

The composition of the present disclosure may include, as appropriate and as necessary, other components-such as aqueous solvents, oily components, anionic surfactants, cationic surfactants, amphoteric surfactants, nonionic surfactants, powders, water-soluble polymers, film-forming agents, UV absorbers, metal ion sequestrant, amino acids, organic amines, polymer emulsions, pH adjusters, skin nutrients, vitamins, antioxidants, antioxidant aids, and perfumes—in amounts that do not inhibit the effects of the present disclosure.

Examples of other components that may be blended are described below. At least one of the following components may be added to the composition of the present disclosure.

Examples of aqueous solvents may include water, alcohols, moisturizers, and mixtures thereof.

With respect to water, water used for such as cosmetics and quasi-pharmaceutical products can be used, including e.g., purified water, ion-exchanged water, and tap water. Depending on the purpose, the aqueous phase may further include a water-soluble alcohol.

Examples of water-soluble alcohols may include at least one type selected from lower alcohols, polyhydric alcohols, polyhydric alcohol polymers, dihydric alcohol alkyl ethers, dihydric alcohol alkyl ethers, dihydric alcohol ether esters, glycerin monoalkyl ethers, sugar alcohols, monosaccharides, oligosaccharides, polysaccharides, and derivatives of the above.

Examples of the lower alcohol may include ethanol, propanol, isopropanol, isobutyl alcohol, t-butyl alcohol, and the like.

Examples of the polyhydric alcohol may include dihydric alcohol (such as ethylene glycol, propylen glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, octylene glycol, etc); trihydric alcohol (such as glycerin, trimethylolpropane, etc); tetrahydric alcohol (such as such as pentaerythritol such as 1,2,6-hexanetriol, etc); pentahydric alcohol (such as xylitol, etc); hexahydric alcohol (such as sorbitol, mannitol, etc); polyhydric alcohol polymer (such as diethylene glycol, dipropylene glycol, triethylene glycol, polypropylene glycol, tetraethylene glycol, diglycerin, polyethylene glycol, triglycerin, tetraglycerin, polyglycerin, etc); dihydric alcohol alkyl ethers (such as ethylene glycol monomethyl ether, ethylene glycol monoethyl ether, ethylene glycol monobutyl ether, ethylene glycol monomphenyl ether, ethylene glycol monohexyl ether, ethylene glycol mono2-methylhexyl ether, ethylene glycol isoamyl ether, ethylene glycol benzil ether, ethylene glycol isopropyl ether, ethylene glycol dimethyl ether, ethylene glycol diethyl ether, ethylene glycol dibutyl ether, etc); dihydric alcohol alkyl ethers (such as diethylene glycol monomethyl ether, diethylene glycol monoethyl ether, diethylene glycol monombutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether, etc); dihydric alcohol ether ethers (such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disaccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate, etc); glycerin monoalkyl ether (such as chimyl alcohol, selachyl alcohol, batyl alcohol, etc); sugar alcohol (such as sorbitol, maltitol, maltotriose, mannitol, sucrose, erythritol, glucose, fructose, starch sugar, maltose, xylitose, starch sugar hydrogenated alcohol, etc); glycolide, tetrahydrofurfuryl alcohol; POE-tetrahydrofurfuryl alcohol; POP/POE-butyl ether; tripolyoxypropylene glycerin ether; POP-glycerin ether; POP-glycerin ether phosphoric acid; POP/POE-pentaerythritol ether; polyglycerin, and the like.

Examples of the monosaccharides may include at least one selected from triose (such as D-glyceryl aldehyde, dihydroxyacetone, etc); tetrose (such as D-erythrose, D-erythrulose, D-threose, erythritol, etc); pentaose (such as L-arabinose, D-xylose, L-lyxose, D-arabinose, D-ribose, D-ribulose, D-xylulose, L-xylulose, etc); hexalose (such as D-glucose, D-talose, D-psicose, D-galactose, D-fructose, L-galactose, L-mannose, D-tagatose, etc); heptose (such as aldoheptose, heplose, etc); octose (such as octulose, etc); deoxy sugar (such as 2-deoxy-D-ribose, 6-deoxy-L-galactose, 6-deoxy-L-mannose, etc); amino sugar (such as D-glucosamine, D-galactosamine, sialic acid, amino uronic acid, muramic acid, etc); uronic acid (such as D-grucuronic acid, D-mannuronic acid, L-guluronic acid, D-garacturonic acid, L-iduronic acid, etc) and the like.

Examples of the oligosaccharide may include at least one selected from sucrose, guntianose, umbelliferose, lactose, planteose, isolignoses, α,α-trehalose, raffinose, lignoses, umbilicin, stachyose, verbascoses, and the like.

Examples of the polysaccharide may include at least one selected from cellulose, quince seed, chondroitinsulfate, starch, galactan, dermatan sulfate, glycogen, acasia gum, heparansulfate, hyaluronan, gum tragacanth, keratan sulfate, chondoroitin, xanthan gum, mucoitin sulfate, guar gum, dextran, keratosulfate, locust bean gum, succinoglycan, caronic acid, and the like.

Examples of other polyols may include at least one polyol selected from polyoxyethylene methyl glucoside (Glucam E-10), polyoxypropylene methyl glucoside (Glucam P-10), and the like.

Examples of the moisturizers may include polyethylene glycol, propylene glycol, glycerin, 1,3-butylene glycol, xylitol, sorbitol, maltitol, chondroitin sulfate, hyaluronic acid, mucoitin sulfate, charonic acid, atelocollagen, cholesteryl 12-hydroxystearate, sodium lactate, bile salt, dl-pyrrolidone carboxylate, alkyleneoxide derivative, short-chain soluble collagen, diglycerin (EO)PO adduct, chestnut rose extract, yarrow extract, melilot extract, and the like.

The content by percentage of the aqueous solvent (including water, alcohols, sugars, and moisturizers) to the mass of the composition is preferably 20% by mass or greater, more preferably 40% by mass or greater. If the content by percentage of the aqueous solvent is low, it will be difficult to obtain a firm feel. The content by percentage of the aqueous solvent to the mass of the composition is preferably 90% by mass or less. If the content by percentage of the aqueous solvent is greater than 90% by mass, usability will deteriorate, and it will also be difficult to obtain a firm feel.

Examples of the oily component that may be used include liquid oils, solid fats, waxes, hydrocarbons, higher fatty acids, higher alcohols, synthetic ester oils, and silicone oils. Herein, the term "oily component" encompasses both oil components and components soluble in oil components.

Examples of the liquid oil that may be used may include avocado oil, camellia oil, turtle oil, macadamia nut oil, corn oil, mink oil, olive oil, rapeseed oil, egg yolk oil, sesame oil, par chic oil, wheat germ oil, southern piece oil, castor oil, linseed oil, safflower oil, cotton seed oil, perilla oil, soybean oil, groundnut oil, brown real oil, torreya oil, rice bran oil, Chinese tung oil, Japanese tung oil, jojoba oil, germ oil, triglycerol, and the like.

Examples of the solid fat that may be used may include cacao butter, coconut oil, horse fat, hydrogenated coconut oil, palm oil, beef tallow, sheep tallow, hydrogenated beef tallow, palm kernel oil, lard, beef bones fat, Japan wax kernel oil, hardened oil, hoof oil, Japan wax, hydrogenated caster oil, and the like.

Examples of the waxes that may be used may include beeswax, candelilla wax, cotton wax, carnauba wax, bayberry wax, insect wax, spermaceti, montan wax, bran wax, lanolin, kapok wax, lanolin acetate, liquid lanolin, sugarcane wax, lanolin fatty acid isopropyl ester, hexyl laurate, reduced lanolin, jojoba wax, hardened lanolin, shellac wax, POE lanolin alcohol ether, POE lanolin alcohol acetate, POE cholesterol ether, lanolin fatty acid polyethylene glycol, POE hydrogenated lanolin alcohol ether, and the like.

Examples of the hydrocarbon oils that may be used may include liquid paraffin, ozocerite, squalane, pristane, paraffin, ceresin. squalene, vaseline, microcrystalline wax, and the like.

Examples of the higher fatty asid that may be used may include lauric acid, myristic acid, palmitic acid, stearic acid, behenic acid, oleic acid, undecylenic acid, tallic acid, isostearic acid, linoleic acid, linolenic acid, eicosapentaenoic acid(EPA), docosahexaenoic acid(DHA) and the like.

Examples of the higher alcohol that may be used may include linear alcohol (such as lauryl alcohol, cetyl alcohol, stearyl alcohol, behenyl alcohol, myristyl alcohol, oleyl alcohol, and cetostearyl alcohol); branched-chain alcohol (such as monostearylglycerin ether (batyl alcohol), 2-decyltetradecinol, lanolin alcohol, cholesterol, phytosterol, hexyldodecanol, isostearyl alcohol, and octyldodecanol) and the like.

Examples of the synthesis ester oils that may be used may include isopropyl myristate, cetyl octanoate, octyldodecyl myristate, isopropyl palmitate, butyl stearate, hexyl laurate, myristyl myristate, decyl oleate, hexyldecyl dimethyl octanoate, cetyl lactate, myristyl lactate, lanolin acetate, isocetyl stearate, isocetyl isostearate, cholesteryl 12-hydroxy stearate, ethylene glycol di-2-ethyl hexanoate, dipenta erythritol fatty acid ester, N-alkyl glycol monoisostearate, neopentyl glycol dicaprate, diisostearyl malate, glyceryl di-2-heptyl undecanoate, trimethyrol propane tri-2-ethyl hexanoate, trimethyrol propane triisostearate, pentaerythritol tetra-2-ethyl hexanoate, glyceryl tri-2-ethyl hexanoate, glyceryl trioctanoate, glyceryl triisopalmitate, trimethyrol propane triisostearate, cetyl 2-ethylhexanoate, 2-ethylhexyl palmitate, glyceryl trimyristate, glyceride tri-2-heptyl undecanoate, castor oil fatty acid methyl ester, oleyl oleate, acetoglyceride, 2-heptyundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, triethyl citrate, and the like.

Examples of the silicone oil that may be used include dimethylpolysiloxane, methylhydrogenpolysiloxane, methylphenylpolysiloxane, stearoxymethylpolysiloxane, polyether-modified organopolysiloxane, fluoroalkyl/polyoxyalkylene co-modified organopolysiloxane, alkyl-modified organopolysiloxane, terminal-modified organopolysiloxane, fluorine-modified organopolysiloxane, amino-modified organopolysiloxane, silicone gel, acrylic silicone, trimethylsiloxysilicic acid, silicone compounds such as silicone RTV rubber, and the like.

The oily component may affect the film-forming of polyisobutene. The content by percentage of the oily component, inclusive of polyisobutene and hydrocarbon oil, to the mass of the composition is preferably 70% by mass or less, more preferably 50% by mass or less, even more preferably 40% by mass or less, for example. If the content of the oily component excesses 70% by mass, dilution of polyisobutene in a preparation takes place. The ability of film-forming of polyisobutene is thus lowered, the user may less likely perceive a firm feel by polyisobutene. The content by percentage of the oily component, inclusive of polyisobutene and hydrocarbon oil, to the mass of the composition is preferably 5% by mass or greater, more preferably 10% by mass or greater, even more preferably 20% by mass or greater, for example. If the content of the oily component is less than 5% by mass, polyisobutene is hard to be spread. A uniform film is thus hard to be formed on the skin, so that the user may less likely perceive a firm feel with polyisobutene.

Examples of the powder bodies may include inorganic powder (such as talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstate, magnesium, silica, zeolite, glass, barium sulfate, calcined calcium sulfate (calcined gypsum), calcium phosphate, fluorine apatite, hydroxyapatite, ceramic powder, metallic soap (such as zinc myristate, calcium palimitate, and aluminum stearate), and boron nitride, etc); organic powder (such as polyamide resin powder (nylon powder), polyethylene powder, polymethylmethacrylate powder, polystyrene powder, styrene-acrylic acid copolymer powder, benzoguanamine resin powder, poly (tetrafluroethylene) powder, and cellulose powder, silicone resin powder, silk powder, wool powder, urethane powder, etc); inorganic white family pigment (such as titanium dioxide, zinc oxide, etc); inorganic red family pigment (such as iron oxide (colcothar), iron titanate, etc); inorganic brown family pigment (such as γ-iron oxide, etc); inorganic yellow family pigment (such as yellow iron oxide, loess, etc); inorganic black family pigment (such as black iron oxide, carbon black, lower titanium oxide, etc); inorganic purple family pigment (such as manganese violet, cobalt violet, etc); inorganic green family pigment (such as chrome oxide, chrome hydroxide, cobalt titanate, etc); inorganic blue family pigment (such as ultramarine, iron blue, etc); pearl pigment (such as titanium oxide coated mica, titanium oxide coated bismuth oxychloride, titanium oxide coated talc, colored titanium oxide coated mica, bismuth oxychloride, argentine, etc); metal powder pigment (such as aluminum powder, copper powder, etc); organic pigment such as zirconium, barium, or aluminum lake (such as organic pigment such as Red No. 201, Red No. 202, Red No. 204, Red No. 205, Red No. 220, Red No. 226, Red No. 228, Red No. 405, Red No. 201, Orange No. 203, Orange No. 204, Yellow No. 205, Yellow No. 401, Blue No. 401, Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1, etc); natural pigment (such as chlorophyll, β-carotene, etc), and the like.

Among the above powder, conventionally known pigments (including extenders) may be used as the pigment. Examples may include inorganic powder such as talc, kaolin, mica, sericite, muscovite, biotite, phlogopite, synthetic mica, silica, zeolite, barium sulfate, calcined calcium sulfate, calcined gypsum, calcium phosphate, fluorine apatite, hydroxyapatite, ceramic powder; inorganic white family pigment such as titanium dioxide, zinc oxide; inorganic red family pigment such as iron oxide (colcothar), iron titanate; inorganic brown family pigment such as γ-iron oxide; inorganic yellow family pigment such as yellow iron oxide, loess; inorganic black family pigment such as black iron oxide, carbon black, lower titanium oxide; inorganic purple family pigment such as manganese violet, cobalt violet; inorganic green family pigment such as chrome oxide, chrome hydroxide, cobalt titanate; inorganic blue family pigment such as ultramarine, iron blue; pearl pigment such as titanium oxide coated mica, titanium oxide coated bismuth oxychloride, titanium oxide coated talc, colored titanium oxide coated mica, bismuth oxychloride, argentine; metal powder pigment such as aluminum powder, copper powder; organic pigment of zirconium, barium, or aluminum lake and etc. such as Red No. 202, Red No. 205, Red No. 220, Red No. 228, Red No. 405, Orange No. 204, Yellow No. 205, Yellow No. 401, Blue No. 404; organic pigment such as Red No. 3, Red No. 104, Red No. 227, Red No. 401, Orange No. 205, Yellow No. 4, Yellow No. 202, Green No. 3, and Blue No. 1, natural pigment such as chlorophyll, 0-carotene; and the like.

The content by percentage of the pigment to the mass of the composition is preferably less than 8% by mass, more preferably 6% by mass or less, more preferably 4% by mass or less, more preferably 2% by mass or less, even more preferably 1% by mass or less. Lowering the content of the pigment can enhance the quality of the film to intensify a firm feel.

Examples of the anionic surfactants that may be used may include fatty acid soap (such as sodium laurate, and sodium palmitate); higher alkyl sulfate ester salt (such as sodium lauryl sulfate, and potassium lauryl sulfate); alkyl ether sulfate ester salt (such as POE-lauryl sulfate triethanolamine, and sodium POE-lauryl sulfate); N-acyl sarcosinic acid (such as sodium lauroyl sarcocinate); higher fatty acid amide sulfonate (such as sodium N-stearoyl-N-methyltaurate, sodium N-myristoyl-N-methyltaurate, sodium methyl cocoyl taurate, and sodium laurylmethyl taurate); phosphate ester salt (sodium POE-oleylether phosphate, and POE-stearylether phosphate); sulfosuccinate (such as sodium di-2-ethylhexyl sulfosuccinate, sodium monolauroyl monoethanolamide polyethylene sulfosuccinate, and sodium lauryl polypropylene glycol sulfosuccinate); alkylbenzene sulfonate (such as sodium linear dodecylbenzene sulfonate, triethanolamine linear dodeylbenzene sulfonate, and linear dodecylbenzene sulfonate); higher fatty acid ester sulfate ester salt (such as sodium hydrogenated gryceryl cocoate sulfate); N-acyl glutamate (such as monosodium N-lauroyl glutamate, disodium N-stearoyl glutamate, and monosodium N-myristoyl-L-glutamate); sulfonated oil (such as Turkey red oil); POE-alkyl ether carboxylic acid; POE-alkyl aryl ether carboxylate;

α-olefine sulfonate; higher fatty acid ester sulfonate; secondary alcohol sulfate ester salt; higher fatty acid alkylolamide sulfate ester salt; sodium lauroyl monoethanolamide succinate; N-palmitoyl asparaginate ditriethanolamine; sodium casein; and the like.

Examples of the cationic surfactants may include alkyltrimethyl ammonium salt (such as stearyltrimethyl ammonium chloride, lauryltrimethyl ammonium chloride); alkylpyridinium salt (such as cetylpyridinium chloride); distearyldimethyl ammonium chloride; dialkyldimethyl ammonium salt; poly (N,N'-dimethyl-3,5-methylenepiperidinium) chloride; alkyl quaternary ammonium salt; alkyldimethylbenzyl ammonium salt; alkylisoquinolinium salt; dialkylmorphonium salt; POE alkylamine; alkylamine salt; polyamine fatty acid derivative; amyl alcohol fatty acid derivative; benzalkonium chloride; benzethonium chloride, and the like.

Examples of the amphoteric surfactant that may be used may include: imidazoline-based amphoteric surfactant (such as sodium 2-undecyl-N,N,N-(hydroxyethylcarboxymethyl)-2-imidazoline and 2-cocoyl-2-imidazolinium hydroxide-1-carboxyethyloxy disodium salt); and betaine-based surfactant (such as 2-heptadecyl-N-carboxymethyl-N-hydroxyethyl imidazolinium betaine, lauryl dimethylaminoacetic acid betaine, alkyl betaine, amidobetaine, and sulfobetaine).

Examples of the lipophilic nonionic surfactants may include sorbitan fatty acid ester (such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2 ethylhexylate, diglycerol sorbitan tetra-2 ethylhexylate, etc); glyceryl polyglyceryl fatty acid (such as glyceryl monocotton oil fatty acid, glyceryl monoerucate, glyceryl sesquioleate, glyceryl monostearate, glyceryl α, α'-oleate pyroglutamate, glyceryl monostearate malate, etc); propylene glycol fatty acid ester (such as propylene glycol monostearate, etc); hydrogenated caster oil derivative; glyceryl alkyl ether, and the like.

Examples of the hydrophilic nonionic surfactants that may be used may include POE sorbitan fatty acid ester (such as POE sorbitan monooleate, POE sorbitan monostearate, POE sorbitan monooleate, POE sorbitan tetraoleate); POE sorbit fatty acid ester (such as POE sorbit monolaurate, POE sorbit monooleate, POE sorbit pentaoleate, POE sorbit monostearate), POE glyceryl fatty acid ester (such as POE monooleate such as POE glyceryl monostearate, POE glyceryl monoisostearate, POE glyceryl triisostearate); POE fatty acid ester (such as POE distearate, POE monodioleate, ethyleneglycol distearate); POE alkyl ether (such as POE lauryl ether, POE oleyl ether, POE stearyl ether, POE behenyl ether, POE-2-octyldodecyl ether, POE cholestanol ether); puluronic type (such as Puluronic), POE/POP alkyl ethers (such as POE/POP cetyl ether, POE/POP 2-decyltetradecyl ether, POE/POP monobutyl ether, POE/POP hydrogenated lanoline, POE/POP glycerin ether); tetra POE/tetra POP ethylenediamine condensation products (such as Tetronic); POE castor oil hydrogenated castor oil derivative (such as POE caster oil, POE hydrogenated caster oil, POE hydrogenated caster oil monoisostearate, POE hydrogenated castor oil triisostearate, POE hydrogenated caster oil monopyroglutamate monoisostearate diester, POE hydrogenated oil maleate); POE beeswax/lanoline derivative (such as POE sorbitol beeswax); alkanolamide (such as coconut oil fatty acid diethanolamide, lauric acid monoethanolamide, fatty acid isopropanolamide); POE propyleneglycol fatty acid ester; POE alkyl amines; POE fatty acid amide; sucrose fatty acid ester; alkylethoxydimethylamine oxide; trioleyl phosphoric acid and the like.

Examples of the natural water-soluble polymer may include plant-based polymer (such as gum Arabic, gum tragacanth, galactan, guar gum, locust bean gum, gum karaya, carrageenan, pectine, agar, quince seed (cydonia oblonga), algae colloid (brown algae extract), starch (rice, corn, potato, wheat), glicyrrhizic acid); microorganism based polymer (such as xanthan gum, dextran, succinoglycan, pullulan, etc), animal-based polymer (such as collagen, casein, albumin, gelatine, etc) and the like.

Examples of the semisynthetic water-soluble polymer may include starch-based polymer (such as carboxymethyl starch, methylhydroxypropyl starch, etc); cellulose-based polymer (such as methylcellulose, ethylcellulose, methylhydroxypropylcellulose, hydroxyethylcellulose, cellulose sodium sulfate, hydroxypropylcellulose, carboxymethylcellulose, sodium calboxymethyl cellulose, crystalline cellulose, cellulose powder, etc); algin acid-based polymer (such as sodium alginate, propylene glycol alginate ester, etc), and the like.

Examples of the synthetic water-soluble polymer may include vinyl based polymer (such as polyvinyl alcohol, polyvinyl methyl ether, polyvinylpyrrolidone, carboxyvinylpolymer, etc); polyoxyethylene based polymer (such as polyoxyethylenepolyoxypropylene copolymer such as polyethylene glycol 20,000, 40,000 and 60,000, etc); acrylic polymer (such as sodium polyacrylate, polyethylacrylate, polyacrylamide, etc); polyethyleneimine; cationic polymer; and the like.

Examples of the film-forming agent may include an anionic film-forming agent (such as (meta)acrylic acid/(meta)acrylic acid ester copolymer, methyl vinyl ether/maleic anhydride coplymer, etc), a cationic film-forming agent (such as cationic cellulose, diallyldimethylammonium chloride polymer, diallyldimethylammonium chloride/acrylic amide copolymer, etc), a nonionc film-forming agent (such as polyvinyl alcohol, polyvinylpyrrolidone, polyvinyl acetate, polyacrylic ester copolymer, (meta)acrylamide, polymeric silicone, silicone resin, trimethylsiloxysilicate, etc), and the like.

Examples of the ultraviolet light absorbers may include benzoic acid family ultraviolet light absorber (such as p-aminobenzoic acid (hereinafter abbreviated as PABA), PABA monoglycerine ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA ethyl ester, etc); anthranilic acid family ultraviolet light absorber (such as homomenthyl N-acetylanthranilate etc); salicylic acid family ultraviolet light absorber (such as amyl salicylate, menthyl salicylate, homomenthyl salicylate, octyl salicylate, phenyl salicylate, benzyl salicylate, p-isopropanolphenyl salicylate, etc); cinnamic acid family ultraviolet light absorber (such as octyl methoxycinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, glyceryl mono-2-ethylhexanoyl-diparamethoxy cinnamate, etc); benzophenone family ultraviolet light absorber (such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, 4-hydroxy-3-carboxybenzophenone, etc); 3-(4'-methylbenzylidene)-d,l-camphor and 3-benzylidene-d,l-camphor; 2-phenyl-5-methylbenzoxazol; 2,2'-hydroxy-5-methylphenylbenzotriazol, 2-(2'-hydroxy-5'-t-octylphenyl) benzotriazol, 2-(2'-hydroxy-5'-methylphenylbenzotriazol; dibenzalazine; dianisoylmethane; 4-methoxy-4'-t-butyldibenzoylmethane; 5-(3,3-dimethyl-2-norbornylidene)-3-pentane-2-one; dimorpholinopyridazinone; 2-ethylhexyl 2-cyano-3,3-diphenylacrylate; 2,4-bis-{[4-(2-ethylhexyloxy)-2-hydroxy]-phenyl}-6-(4-methoxyphenyl)-(1,3,5)-triazine, and the like.

Examples of the metal ion sequestrant may include 1-hydroxyethane-1, 1-diphosphonic acid, 1-hydroxyethane, 1-diphosphonic acid 4Na salt, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, trisodium hydroxyethyl ethylenediamine triacetate, and the like.

Examples of the amino acid may include neutral amino acid (such as threonine, cysteine, etc); basic amino acid (such as hydroxylysine, etc) and the like. Examples of the amino acid derivative may include sodium acyl sarcosinate (sodium lauroyl sarcosinate), acyl glutamate, sodium acyl 0-alanine, glutathione, pyrrolidone carboxylate, and the like.

Examples of the organic amine may include monoethanolamine, diethanolamine, triethanolamine, morpholine, triisopropanolamine, 2-amino-2-methyl-1,3-propanediol, 2-amino-2-methyl-1-propanol, and the like.

Examples of the polymer emulsion may include acrylic resin emulsion, ethyl polyacrylate emulsion, solution of acrylic resin, polyacrylalkylester emulsion, polyvinyl acetate resin emulsion, natural rubber latex, and the like.

Examples of the pH modifier may include buffer such as lactic acid-sodium lactate, citric acid-sodium citrate, succinic acid-sodium succinate, and the like.

Examples of the vitamins may include vitamine A, B1, B2, B6, C, E and derivatives thereof, pantothenic acid and derivatives thereof, biotin, and the like.

Examples of the anti-oxidant may include tocopherols, dibutyl hydroxy toluene, butyl hydroxy anisole, and gallic acid esters, and the like.

Examples of the anti-oxidant aid may include phosphoric acid, citric acid, ascorbic acid, maleic acid, malonic acid, succinic acid, fumaric acid, cephalin, hexamethaphosphate, phytic acid, ethylenediaminetetraacetic acid, and the like.

Examples of other containable compositions may include an antiseptic agent (such as ethylparaben, butylparaben, chlorphenesin, 2-phenoxyethanol, etc); antiphlogistic (such as glycyrrhizinic acid derivatives, glycyrrhetic acid derivatives, salicylic acid derivatives, hinokitiol, zinc oxide, allantoin, etc); a skin-whitening agent (such as placental extract, saxifrage extract, arbutin, etc); various extracts (such as phellodendron bark (cork tree bark), coptis rhizome, lithospermum, peony, swertia herb, birch, sage, loquat, carrot, aloe, mallow, iris, grape, coix seed, sponge gourd, lily, saffron, cnidium rhizome, ginger, hypericum, restharrow, garlic, red pepper, citrus unshiu, Japanese angelica, seaweed, etc); an activator (such as royal jelly, photosenstizer, cholesterol derivatives, etc); a blood circulation promotion agent (such as nonylic acid vanillylamide, nicotine acid benzyl ester, nicotine acid β-butoxyethyl ester, capsaicin, zingerone, cantharides tincture, ichthammol, tannic acid, α-borneol, tocopheryl nicotinate, meso-inositol hexanicotinate, cyclandelate, cinnarizine, tolazoline, acetylcholine, verapamil, cepharanthine, γ-oryzanol, etc); an antiseborrheric agent, (such as sulfur, thianthl, etc); an anti-inflammatory agent (such as tranexamic acid, thiotaurine, hypotaurine, etc), and the like.

The composition of the present disclosure further may inculde, as necessary, caffeine, tannin, verapamil, tranexamic acid and derivatives thereof; various crude drug extracts such as licorice, Chinese quince, Pyrola japonica and the like; drugs such as tocopherol acetate, glycyrrhetinic acid, glycyrrhizic acid and derivatives thereof, or salts thereof; skin-whitening agents such as vitamin C, magnesium ascorbyl phosphate, ascorbic acid glucoside, arbutin, kojic acid and the like; amino acids such as arginine and lysine and the like and derivatives thereof.

The viscosity of the composition of the present disclosure is preferably 2,000 mPa·s or higher. In cases where the composition is a cream, the viscosity is preferably 20,000 mPa·s or higher. If the viscosity is too low, it will be difficult to provide a sufficient firm feel. The viscosity can be measured with a Brookfield-type viscometer (spindle No. 6 or 7; rotation speed: 10 rpm) at 30° C.

The composition of the present disclosure is suitably applicable to cosmetics. Particularly, the composition of the present disclosure is suitably applicable to a cosmetic to be applied with the hand. Particularly, the composition of the present disclosure is suitably applicable to a cosmetic to be applied to the skin. For example, the composition of the present disclosure is suitable for application by rubbing the composition onto the skin. Thereby, the user can feel skin firmness and obtain a sense of swift finish of the composition on the skin.

Particularly, the composition of the present disclosure is suitably applicable to the face (except for the lips). For example, the composition of the present disclosure can be applied around/near the eyes. Particularly, the composition of the present disclosure can suitably be applied outside the lower eyelids (for example, in the vicinity of the eye bags). By using the composition of the present disclosure on the face (particularly around/near the eyes), the user can feel skin firmness more intensely (more favorably).

The composition of the present disclosure can be used as an external (dermatological) preparation for providing a firm feel to the skin. In this case, making the composition into an external preparation for skin that is used by being rubbed onto the skin can offer the user a more intense firm feel.

The expression "skin firmness (skin resilience)" or "firm feel (resilient feel)" as used in the present disclosure refers to the sensation, upon use, obtained during and/or after applying the composition to the skin, wherein the skin is moderately firm without sagging or feeling tight. It is considered that the firm feel obtained by the composition of the present disclosure is created as a result of the polyisobutene forming a film on the skin during, and after, application of the composition to the skin.

With the composition of the present disclosure, stickiness felt by the user can be suppressed, even when the composition of the present disclosure is applied to the skin. Further, the composition of the present disclosure has emulsion stability.

The composition of the present disclosure has a bitter taste, so that it is preferred that the user does not apply the composition of the present disclosure to the lips when the bitter taste is not comfortable for the user.

Methods for producing the emulsion composition for skin of the present disclosure will be described. The emulsion composition for skin of the present disclosure can be prepared according to generally known methods, without being limited to a specific method. For example, the emulsion composition for skin can be prepared by mixing each of the aforementioned components. The polyisobutene may be added after being dissolved into a hydrocarbon oil.

Example 1

Examples of the composition of the present disclosure will be described below. The composition of the present disclosure, however, is not limited to the following examples. The unit employed for indicating the content by percentage shown in the Tables is percent by mass (mass %).

Compositions having the respective formulations shown in the Tables below were prepared, and the firm feel, lack of stickiness, and emulsion stability were evaluated.

Firm Feel:

Twenty female panelists applied each test sample onto her upper arm portion with the hand, and were inquired about the firm feel of the skin after application, to evaluate each test sample according to the following criteria.
  AA: 16 or more panelists answered that the skin felt firm after application.
  A: 12 to 15 panelists answered that the skin felt firm after application.
  B: 8 to 11 panelists answered that the skin felt firm after application.
  C: 7 or fewer panelists answered that the skin felt firm after application.

Lack of Stickiness:

Twenty female panelists applied each test sample onto her upper arm portion with the hand, and were inquired about the stickiness after application, to evaluate each test sample according to the following criteria.
  AA: 16 or more panelists answered that there was no stickiness or sliminess.
  A: 12 to 15 panelists answered that there was no stickiness or sliminess.
  B: 8 to 11 panelists answered that there was no stickiness or sliminess.
  C: 7 or fewer panelists answered that there was no stickiness or sliminess.

Emulsion Stability:

Each test sample was being kept at 50° C. for 4 weeks and then cooled to room temperature, of which state with regard to each test sample was visually evaluated according to the following criteria.
  A: No abnormality.
  B: Slight separation is observed.
  C: Separation is observed.

Test Examples 1 to 4

In Test Examples 1 to 4, the effects obtained by including or not including polyisobutene were verified. Tables 1 and 2 show the compositions and results. The compositions according to Test Examples 1 to 4 were oil-in-water-type compositions. The compositions according to Test Examples 1 and 3 included polyisobutene having a relative mass (molecular weight) of around 55,000. The polyisobutene was added in a form dissolved in isododecane. On the other hand, the compositions according to Test Examples 2 and 4 did not include polyisobutene. The compositions according to Test Examples 1 and 2 had similar compositions except for polyisobutene. The compositions according to Test Examples 3 and 4 had similar compositions except for polyisobutene.

When comparing the composition according to Test Example 1 with the composition according to Test Example 2, no different was found in terms of lack of stickiness and emulsion stability. Similarly, when comparing the composition according to Test Example 3 with the composition according to Test Example 4, no different was found in terms of lack of stickiness and emulsion stability. However, in terms of firm feel, Test Examples 1 and 3, including polyisobutene, were able to obtain higher ratings than Test Examples 2 and 4 including no polyisobutene. Thus, it is considered that polyisobutene contributes to the firmness felt by the user.

TABLE 1

| | | Test Example | 1 | 2 |
|---|---|---|---|---|
| (1) | Water | Ion-exchanged Water | Balance | Balance |
| (2) | Moisturizer | Glycerin | 5 | 5 |
| (3) | | 1,3-Butylene Glycol | 5 | 5 |
| (4) | Thickener | Carboxyvinylpolymer | 0.15 | 0.15 |
| (5) | Neutralizer | Potassium Hydroxide | 0.1 | 0.1 |
| (6) | Surfactant | PEG-60 Glyceryl Isostearate | 1 | 1 |
| (7) | | PEG-5 Glyceryl Stearate | 1 | 1 |
| (8) | Oily | Behenyl Alcohol | 0.3 | 0.3 |
| (9) | Component | Batyl Alcohol | 0.3 | 0.3 |
| (10) | | Pentaerythritol Tetra-2-ethylhexanoate | 1 | 1 |
| (11) | | Dimethicone | 2 | 2 |
| (12) | | Hydrogenated Polydecene | 5 | 5 |
| (13) | | Isododecane | 1.5 | — |
| (14) | | Polyisobutene (Molecular Weight 55,000) *1 | 0.5 | — |
| (15) | Antiseptic | Phenoxyethanol | 0.5 | 0.5 |
| (16) | Chelating Agent | Sodium Metaphosphate | 0.03 | 0.03 |
| | | Total | 100 | 100 |
| Evaluation | Firm feel | | A | C |
| | Lack of stickiness | | A | A |
| | Emulsion stability | | A | A |

*1: Oppanol B12SFN BASF

TABLE 2

| | Test Example | | 3 | 4 |
|---|---|---|---|---|
| (1) | Water | Ion-exchanged Water | Balance | Balance |
| (2) | Moisturizer | Glycerin | 10 | 10 |
| (3) | | 1,3-Butylene Glycol | 5 | 5 |
| (4) | | Maltitol | 3 | 3 |
| (5) | | Xylitol | 1 | 1 |
| (6) | Thickener | Xanthan Gum | 0.1 | 0.1 |
| (7) | Neutralizer | Arginine | 0.1 | 0.1 |
| (8) | Surfactant | Ceteth-25 | 1.5 | 1.5 |
| (9) | | PEG-5 Glycery Stearate | 1.5 | 1.5 |
| (10) | | Glyceryl Stearate SE | 1.5 | 1.5 |
| (11) | Oily | Behenic Acid | 0.1 | 0.1 |
| (12) | Component | Stearyl Alcohol | 2 | 2 |
| (13) | | Batyl Alcohol | 0.5 | 0.5 |
| (14) | | Microcrystalline Wax | 6 | 6 |
| (15) | | Beeswax | 3 | 3 |
| (16) | | Petrolatum | 5 | 5 |
| (17) | | Squalane | 32 | 40 |
| (18) | | Isododecane | 6 | — |
| (19) | | Polyisobutene (Molecular Weight 55,000) *1 | 2 | — |
| (20) | Antiseptic | Phenoxyethanol | 0.5 | 0.5 |
| (21) | Chelating Agent | Sodium Metaphosphate | 0.03 | 0.03 |
| (22) | Perfume | Perfume | q.s. | q.s. |
| | | Total | 100 | 100 |
| Evaluation | Firm feel | | A | C |
| | Lack of stickiness | | A | A |
| | Emulsion stability | | A | A |

Test Examples 5 to 7

In Test Examples 5 to 7, differences in the effects of polyisobutene and hydrogenated polyisobutene were verified. Tables 3 and 4 show the compositions and results. The compositions according to Test Examples 5 to 7 were oil-in-water-type compositions. The composition according to Test Example 5 included polyisobutene having a relative mass (molecular weight) of around 55,000. On the other hand, the compositions according to Test Examples 6 and 7 included hydrogenated polyisobutene instead of polyisobutene. The compositions according to Test Examples 5 to 7 had similar compositions other than polyisobutene and hydrogenated polyisobutene.

With the composition according to Test Example 6, including hydrogenated polyisobutene with a molecular weight of 1000, the user could not feel firmness, but instead felt stickiness. With the composition according to Test Example 7 which included hydrogenated polyisobutene with a molecular weight of 2850, the user was able to feel firmness, but felt stickiness. In contrast, with the composition according to Test Example 5, including polyisobutene, the user was able to feel firmness without feeling stickiness. Thus, it is considered that polyisobutene is more effective than hydrogenated polyisobutene in order to achieve both providing firm feel and no stickiness.

In Test Example 5, applying the composition was finished more swiftly than Test Example 1, and a firm feel with better quality was achieved. Thus, it is considered that, it is possible to improve both the feel upon use and the quality of the firm feel by employing polyisobutene and a silicone elastomer in combination.

TABLE 3

| | Test Example | | 5 | 6 | 7 |
|---|---|---|---|---|---|
| (1) | Water | Ion-exchanged Water | Balance | Balance | Balance |
| (2) | Moisturizer | Glycerin | 10 | 10 | 10 |
| (3) | | 1,3-Butylene Glycol | 10 | 10 | 10 |
| (4) | | Trehalose | 2 | 2 | 2 |
| (5) | Thickener | Acrylates/Steareth-20 Methacrylate Copolymer | 0.2 | 0.2 | 0.2 |
| (6) | | PEG-240/HDI Copolymer Bis-Decyltetradeceth-20 Ether | 0.2 | 0.2 | 0.2 |
| (7) | | Dimethylacrylamide/Sodium Acryloyldimethyltaurate Crosspolymer | 0.5 | 0.5 | 0.5 |
| (8) | Neutralizer | Potassium Hydroxide | 0.03 | 0.03 | 0.03 |
| (9) | Surfactant | PEG-40 Stearate | 0.5 | 0.5 | 0.5 |
| (10) | | Glyceryl Stearate SE | 1 | 1 | 1 |
| (11) | Oily | Stearyl Alcohol | 1 | 1 | 1 |
| (12) | Component | Behenyl Alcohol | 1 | 1 | 1 |
| (13) | | Batyl Alcohol | 1 | 1 | 1 |
| (14) | | Pentaerythrityl Tetrabehenate/ Benzoate/Ethylhexanoate | 2 | 2 | 2 |
| (15) | | Petrolatum | 3 | 3 | 3 |

TABLE 3-continued

| | | Test Example | 5 | 6 | 7 |
|---|---|---|---|---|---|
| (16) | | Liquid Paraffin | 5 | 5 | 5 |
| (17) | | Pentaerythrityl Tetraethylhexanoate | 3 | 3 | 3 |
| (18) | | Isododecane | 1 | — | — |
| (19) | | Polyisobutene (Molecular Weigh 55,000) *1 | 0.25 | — | — |
| (20) | | Hydrogenated Polyisobutene (Molecular Weight 1,000) | — | 1 | — |
| (21) | | Hydrogenated Polyisobutene (Molecular Weight 2,850) | — | — | 1 |
| (22) | | Dimethicone | 10 | 10 | 10 |
| (23) | Elastomer | Dimethicone Crosspolymer | 2 | 2 | 2 |
| (24) | Powder | Titanium Dioxide | 1 | 1 | 1 |
| (25) | | Silica | 1 | 1 | 1 |
| (26) | | HDI/Trimethylol Hexyllactone Crosspolymer | 1 | 1 | 1 |
| (27) | Dispersing Agent | Sodium Metaphosphate | 0.05 | 0.05 | 0.05 |
| (28) | Chelating Agent | Ethylenediaminetetraacetic Acid Trisodium Salt Dihydrate | 0.1 | 0.1 | 0.1 |
| (29) | Antiseptic | Phenoxyethanol | 0.5 | 0.5 | 0.5 |
| (30) | Perfume | Perfume | q.s. | q.s. | q.s. |
| | | Total | 100 | 100 | 100 |
| Evaluation | Firm feel | | AA | C | A |
| | Lack of stickiness | | A | B | C |
| | Emulsion stability | | A | A | A |

Test Examples 81 to 11

In Test Examples 8 to 11, differences in the effects caused by changing the molecular weight of the polyisobutene were verified. Table 4 shows the compositions and results. The compositions according to Test Examples 8 to 11 were oil-in-water-type compositions. Test Examples 8 to 11 were prepared so that the amount of isododecane therein was the same. With the compositions according to Test Examples 8 to 11, many of the users were able to feel firmness. However, with Test Example 11 using polyisobutene with a molecular weight of 200,000, the users felt stickiness, and it failed to achieve emulsion stability. In contrast, with Test Examples 8 to 10 using polyisobutenes with molecular weights from 40,000 to 85,000, it was possible to achieve both emulsion stability and lack of stickiness. Thus, it is considered that the molecular weight of the polyisobutene is preferably less than 200,000, more preferably 150,000 or less, even more preferably 100,000 or less. Further, the molecular weight of the polyisobutene is preferably 20,000 or greater, more preferably 30,000 or greater.

TABLE 4

| | | Test Example | 8 | 9 | 10 | 11 |
|---|---|---|---|---|---|---|
| (1) | Water | Ion-exchanged-Water | Balance | Balance | Balance | Balance |
| (2) | Moisturizer | Glycerin | 10 | 10 | 10 | 10 |
| (3) | | 1,3-Butylene Glycol | 10 | 10 | 10 | 10 |
| (4) | | Trehalose | 2 | 2 | 2 | 2 |
| (5) | Thickener | Acrylates/Steareth-20 Methacrylate Copolymer | 0.2 | 0.2 | 0.2 | 0.2 |
| (6) | | PEG-240/HDI Copolymer Bis-Decyltetradeceth-20 Ether | 0.2 | 0.2 | 0.2 | 0.2 |
| (7) | | Dimethylacrylamide/Sodium Acryloyldimethyltaurate Crosspolymer | 0.5 | 0.5 | 0.5 | 0.5 |
| (8) | Neutralizer | Potassium Hydroxide | 0.03 | 0.03 | 0.03 | 0.03 |
| (9) | Surfactant | PEG-40 Stearate | 0.5 | 0.5 | 0.5 | 0.5 |
| (10) | | Glyceryl Stearate SE | 1 | 1 | 1 | 1 |
| (11) | Oily | Stearyl Alcohol | 1 | 1 | 1 | 1 |
| (12) | Component | Behenyl Alcohol | 1 | 1 | 1 | 1 |
| (13) | | Batyl Alcohol | 1 | 1 | 1 | 1 |
| (14) | | Pentaerythrityl Tetrabehenate/Benzoate/Ethylhexanoate | 2 | 2 | 2 | 2 |
| (15) | | Petrolatum | 3 | 3 | 3 | 3 |
| (16) | | Liquid Paraffin | 5 | 5 | 5 | 5 |
| (17) | | Pentaerythrityl Tetraethylhexanoate | 3 | 3 | 3 | 3 |
| (18) | | Isododecane | 3.75 | 3.75 | 3.75 | 3.75 |
| (19) | | Polyisobutene (Molecular Weight 40,000) *2 | 0.25 | — | — | — |
| (20) | | Polyisobutene (Molecular Weight 55,000) *1 | — | 0.25 | — | — |
| (21) | | Polyisobutene (Molecular Weight 85,000) *3 | — | — | 0.25 | — |
| (22) | | Polyisobutene (Molecular Weight 200,000) *4 | — | — | — | 0.25 |
| (23) | | Dimethicone | 10 | 10 | 10 | 10 |
| (24) | Elastomer | Dimethicone Crosspolymer | 2 | 2 | 2 | 2 |
| (25) | Powder | Titanium Dioxide | 1 | 1 | 1 | 1 |
| (26) | | Silica | 1 | 1 | 1 | 1 |

TABLE 4-continued

| | | Test Example | 8 | 9 | 10 | 11 |
|---|---|---|---|---|---|---|
| (27) | | HDI/Trimethylol Hexyllactone Crosspolymer | 1 | 1 | 1 | 1 |
| (28) | Dispersing Agent | Sodium Metaphosphate | 0.05 | 0.05 | 0.05 | 0.05 |
| (29) | Chelating Agent | Ethylenediaminetetraacetic Acid Trisodium Salt Dihydrate | 0.1 | 0.1 | 0.1 | 0.1 |
| (30) | Antiseptic | Phenoxyethanol | 0.5 | 0.5 | 0.5 | 0.5 |
| (31) | Perfume | Perfume | q.s. | q.s. | q.s. | q.s. |
| | | Total | 100 | 100 | 100 | 100 |
| Evaluation | Firm feel | | AA | AA | AA | AA |
| | Lack of stickiness | | A | A | A | B |
| | Emulsion stability | | A | A | A | C |

*2: Oppanol B10SFN BASF
*3: Oppanol B15SFN BASF
*4: Oppanol B30SFN BASF

Test Examples 12 to 14

In Test Examples 12 to 14, the content by percentage of the polyisobutene was varied, to verify the differences in the effects thereof. Table 5 shows the compositions and results. The compositions according to Test Examples 12 to 14 were oil-in-water-type compositions. With Test Examples 12 to 14, it was possible to achieve excellent results in terms of firm feel, lack of stickiness, and emulsion stability. Thus, when taking into consideration all of Test Examples 8 to 14 and Test Examples 1, 3, and 5, it is considered that the content by percentage of polyisobutene is preferably at least 0.2% by mass or greater, more preferably 0.25% by mass or greater. Further, it is considered that the content by percentage of polyisobutene is preferably 2.5% by mass or less, more preferably 2% by mass or less. Particularly, it is considered that, in order to further suppress stickiness, the content by percentage of polyisobutene is preferably 0.4% by mass or less, more preferably 0.3% by mass or less. It is considered that, since Test Example 12 did not include trehalose, Test Example 12 was able to achieve a better result in terms of lack of stickiness compared to Test Example 5.

TABLE 5

| | | Test Example | 12 | 13 | 14 |
|---|---|---|---|---|---|
| (1) | Water | Ion-exchanged Water | Balance | Balance | Balance |
| (2) | Moisturizer | Glycerin | 10 | 10 | 10 |
| (3) | | 1,3-Butylene Glycol | 10 | 10 | 10 |
| (4) | Thickener | Acrylates/Steareth-20 Methacrylate Copolymer | 0.2 | 0.2 | 0.2 |
| (5) | | PEG-240/HDI Copolymer Bis-Decyltetradeceth-20 Ether | 0.2 | 0.2 | 0.2 |
| (6) | | Dimethylacrylamide/Sodium Acryloyldimethyltaurate Crosspolymer | 0.5 | 0.5 | 0.5 |
| (7) | Neutralizer | Potassium Hydroxide | 0.03 | 0.03 | 0.03 |
| (8) | Surfactant | PEG-40 Stearate | 0.5 | 0.5 | 0.5 |
| (9) | | Glyceryl Stearate SE | 1 | 1 | 1 |
| (10) | Oily | Stearyl Alcohol | 1 | 1 | 1 |
| (11) | Component | Behenyl Alcohol | 1 | 1 | 1 |
| (12) | | Batyl Alcohol | 1 | 1 | 1 |
| (13) | | Pentaerythrityl Tetrabehenate/Benzoate/Ethylhexanoate | 2 | 2 | 2 |
| (14) | | Petrolatum | 3 | 3 | 3 |
| (15) | | Liquid Paraffin | 5 | 5 | 5 |
| (16) | | Pentaerythrityl Tetraethylhexanoate | 3 | 3 | 3 |
| (17) | | Isododecane | 1 | 1.5 | 2 |
| (18) | | Polyisobutene (Molecular Weight 55,000) *1 | 0.25 | 0.5 | 0.75 |
| (19) | | Dimethicone | 10 | 10 | 10 |
| (20) | Elastomer | Dimethicone Crosspolymer | 2 | 2 | 2 |
| (21) | Powder | Titanium Dioxide | 1 | 1 | 1 |
| (22) | | Silica | 1 | 1 | 1 |
| (23) | | HDI/Trimethylol Hexyllactone Crosspolymer | 1 | 1 | 1 |
| (24) | Dispersing Agent | Sodium Metaphosphate | 0.05 | 0.05 | 0.05 |

TABLE 5-continued

| | | Test Example | 12 | 13 | 14 |
|---|---|---|---|---|---|
| (25) | Chelating Agent | Ethylenediaminetetraacetic Acid Trisodium Salt Dihydrate | 0.1 | 0.1 | 0.1 |
| (26) | Antiseptic | Phenoxyethanol | 0.5 | 0.5 | 0.5 |
| (27) | Perfume | Perfume | q.s. | q.s. | q.s. |
| | | Total | 100 | 100 | 100 |
| Evaluation | Firm feel | | AA | AA | AA |
| | Lack of stickiness | | AA | A | A |
| | Emulsion stability | | A | A | A |

Test Examples 15 to 19

In Test Examples 15 to 19, the content by percentage of the elastomer was varied, to verify the differences in the effects thereof. The compositions according to Test Examples 15 to 19 were oil-in-water-type compositions. Table 6 shows the compositions and results. The aforementioned Test Example 5 is an example corresponding to Test Examples 15 to 19 with a different content by percentage of the elastomer.

The composition according to Test Example 15 including no elastomer was able to achieve good results in all evaluation items. Stated differently, even without including an elastomer, it was possible to achieve firmness by the polyisobutene while suppressing stickiness. Further, with Test Example 16 including 0.5% by mass of an elastomer, the number of users that felt firmness and lack of stickiness was greater compared to Test Example 15. Thus, it is considered that it was possible to further intensify firmness while further suppressing stickiness by a synergistic effect between the polyisobutene and the elastomer. It is considered that the content by percentage of the elastomer to the mass of the composition is preferably 0.1% by mass or greater, more preferably 0.2% by mass or greater, even more preferably 0.3% by mass or greater, further more preferably 0.4% by mass or greater.

On the other hand, an increase in the addition amount of the elastomer resulted in a decrease in the number of users that felt firmness—although there was also a decrease in the number of users that felt stickiness—and also emulsion stability tended to deteriorate. Thus, it is considered that the content by percentage of the elastomer to the mass of the composition is preferably 6% by mass or less, more preferably 5% by mass or less, even more preferably 4% by mass or less.

TABLE 6

| | | Test Example | 15 | 16 | 17 | 18 | 19 |
|---|---|---|---|---|---|---|---|
| (1) | Water | Ion-exchanged Water | Balance | Balance | Balance | Balance | Balance |
| (2) | Moisturizer | Glycerin | 10 | 10 | 10 | 10 | 10 |
| (3) | | 1,3-Butylene Glycol | 10 | 10 | 10 | 10 | 10 |
| (4) | | Trehalose | 2 | 2 | 2 | 2 | 2 |
| (5) | Thickener | Acrylates/Steareth-20 Methacrylate Copolymer | 0.2 | 0.2 | 0.2 | 0.2 | 0.2 |
| (6) | | PEG-240/HDI Copolymer Bis-Decyltetradeceth-20 Ether | 0.2 | 0.2 | 0.2 | 0.2 | 0.2 |
| (7) | | Dimethylacrylamide/Sodium Acryloyldimethyltaurate Crosspolymer | 0.5 | 0.5 | 0.5 | 0.5 | 0.5 |
| (8) | Neutralizer | Potassium Hydroxide | 0.03 | 0.03 | 0.03 | 0.03 | 0.03 |
| (9) | Surfactant | PEG-40 Stearate | 0.5 | 0.5 | 0.5 | 0.5 | 0.5 |
| (10) | | Glyceryl Stearate SE | 1 | 1 | 1 | 1 | 1 |
| (11) | Oily Component | Stearyl Alcohol | 1 | 1 | 1 | 1 | 1 |
| (12) | | Behenyl Alcohol | 1 | 1 | 1 | 1 | 1 |
| (13) | | Batyl Alcohol | 1 | 1 | 1 | 1 | 1 |
| (14) | | Pentaerythrityl Tetrabehenate/Benzoate/Ethylhexanoate | 2 | 2 | 2 | 2 | 2 |
| (15) | | Petrolatum | 3 | 3 | 3 | 3 | 3 |
| (16) | | Liquid Paraffin | 5 | 5 | 5 | 5 | 5 |
| (17) | | Pentaerythrityl Tetraethylhexanoate | 3 | 3 | 3 | 3 | 3 |
| (18) | | Isododecane | 0.75 | 0.75 | 0.75 | 0.75 | 0.75 |
| (19) | | Polyisobutene (Molecular Weight 55,000) *1 | 0.25 | 0.25 | 0.25 | 0.25 | 0.25 |
| (20) | | Dimethicone | 5 | 5 | 10 | 30 | 30 |
| (21) | Elastomer | Dimethicone Crosspolymer | — | 0.5 | 2 | 5 | 7 |
| (22) | Powder | Titanium Dioxide | 1 | 1 | 1 | 1 | 1 |
| (23) | | Silica | 1 | 1 | 1 | 1 | 1 |
| (24) | | HDI/Trimethylol Hexyllactone Crosspolymer | 1 | 1 | 1 | 1 | 1 |
| (25) | Dispersing Agent | Sodium Metaphosphate | 0.05 | 0.05 | 0.05 | 0.05 | 0.05 |
| (26) | Chelating Agent | Ethylenediaminetetraacetic Acid Trisodium Salt Dihydrate | 0.1 | 0.1 | 0.1 | 0.1 | 0.1 |

TABLE 6-continued

| | Test Example | | 15 | 16 | 17 | 18 | 19 |
|---|---|---|---|---|---|---|---|
| (27) | Antiseptic | Phenoxyethanol | 0.5 | 0.5 | 0.5 | 0.5 | 0.5 |
| (28) | Perfume | Perfume | q.s. | q.s. | q.s. | q.s. | q.s. |
| | | Total | 100 | 100 | 100 | 100 | 100 |
| Evaluation | Firm feel | | B | AA | AA | A | B |
| | Lack of stickiness | | B | A | A | AA | AA |
| | Emulsion stability | | A | A | A | B | C |

Test Examples 20 to 22

Each of the oil-in-water emulsion compositions for skin of the present disclosure was subjected to the same sensory evaluations as described above, and also, the coefficient of kinetic friction was measured. From the trend in change over time of the coefficient of kinetic friction and the magnitude of the value of the coefficient, it is possible to evaluate the firmness felt by the user. The method for measuring the coefficient of kinetic friction is described below. The compositions of Test Examples 20 to 22 were oil-in-water-type compositions. Table 7 shows the compositions and results. FIG. 1 shows the measurement results of the coefficient of kinetic friction.

Measurement of Average Coefficient of Kinetic Friction:

On a piece of artificial leather (Supplale from Idemitsu Technofine Co., Ltd.) was placed 2 μL/cm² of each composition according to Test Examples 20 to 22, and the average coefficient of kinetic friction of each sample coating film was measured with a Handy Tribo Master (TL201 Ts from Trinity-Lab Inc.) under the following conditions: movement speed: 500 mm/minute; measurement distance: 50 mm (outward path); load: 50 g/cm².

In the composition according to Test Example 20, including neither the polyisobutene nor the thickener of component (7) including a 2-acrylamido-2-methyl sulfonic acid component, the coefficient of kinetic friction decreased over time. A decrease in the coefficient of kinetic friction over time indicates that slipping occurs while the user is rubbing the composition into the skin, and thus, the user cannot feel firmness. In fact, there were few users that felt firmness on the sensory evaluation of Test Example 20.

In the composition according to Test Example 21, including polyisobutene and no thickener of component (7), the coefficient of kinetic friction increased over time. An increase in the coefficient of kinetic friction over time indicates that the resistance increases while the user is rubbing the composition into the skin, and thus, the user can perceive that the firm feel is becoming stronger. In fact, many users felt firmness on the sensory evaluation of Test Example 21.

In the composition according to Test Example 22, including both polyisobutene and the thickener of component (7), the coefficient of kinetic friction was higher than each coefficient of Test Examples 20 and 21, and the high coefficient of kinetic friction was maintained over time. A high coefficient of kinetic friction indicates a strong firm feel, and thus, the user can continuously perceive a strong firm feel from the start of the rubbing of the composition onto the skin. In fact, among Test Examples 19 to 22, Test Example 22 had the greatest number of users that felt firmness.

In Test Example 20, it is considered that, although the coefficient of kinetic friction becomes somewhat high due to the effect of the elastomer, the users cannot feel firmness because the composition does not include the polyisobutene and thus slipping occurs. In Test Example 21, it is considered that the coefficient of kinetic friction can be increased over time due to polyisobutene included therein, and thus, the users can perceive a firm feel. In Test Example 22, it is considered that, by employing, in combination, a 2-acrylamido-2-methyl sulfonic acid-based thickener together with the polyisobutene and the elastomer, the coefficient of kinetic friction becomes extremely high, and thus, many users can feel firmness. Thus, it is considered that the 2-acrylamido-2-methyl sulfonic acid-based thickener has an action of enhancing the effects of polyisobutene and the elastomer.

TABLE 7

| | | Test Example | 20 | 21 | 22 |
|---|---|---|---|---|---|
| (1) | Water | Ion-exchanged Water | Balance | Balance | Balance |
| (2) | Moisturizer | Glycerin | 10 | 10 | 10 |
| (3) | | 1,3-Butylene Glycol | 10 | 10 | 10 |
| (4) | | Trehalose | 2 | 2 | 2 |
| (5) | Thickener | Acrylates/Steareth-20 Methacrylate Copolymer | 0.2 | 0.2 | 0.2 |
| (6) | | PEG-240/HDI Copolymer Bis-Decyltetradeceth-20 Ether | 0.2 | 0.2 | 0.2 |
| (7) | | Dimethylacrylamide/Sodium Acryloyldimethyltaurate Crosspolymer | — | — | 0.5 |
| (8) | Neutralizer | Potassium Hydroxide | 0.03 | 0.03 | 0.03 |
| (9) | Surfactant | PEG-40 Stearate | 0.5 | 0.5 | 0.5 |
| (10) | | Glyceryl Stearate SE | 1 | 1 | 1 |
| (11) | Oily | Stearyl Alcohol | 1 | 1 | 1 |
| (12) | Component | Behenyl Alcohol | 1 | 1 | 1 |
| (13) | | Batyl Alcohol | 1 | 1 | 1 |
| (14) | | Pentaerythrityl Tetrabehenate/Benzoate/Ethylhexanoate | 2 | 2 | 2 |
| (15) | | Petrolatum | 3 | 3 | 3 |

TABLE 7-continued

|  |  | Test Example | 20 | 21 | 22 |
|---|---|---|---|---|---|
| (16) |  | Liquid Paraffin | 5 | 5 | 5 |
| (17) |  | Pentaerythrityl Tetraethylhexanoate | 3 | 3 | 3 |
| (18) |  | Isododecane | — | 0.75 | 0.75 |
| (19) |  | Polyisobutene (Molecular Weight 55,000) *1 | — | 0.25 | 0.25 |
| (20) |  | Dimethicone | 10 | 10 | 10 |
| (21) | Elastomer | Dimethicone Crosspolymer | 2 | 2 | 2 |
| (22) | Powder | Titanium Dioxide | 1 | 1 | 1 |
| (23) |  | Silica | 1 | 1 | 1 |
| (24) |  | HDI/Trimethylol Hexyllactone Crosspolymer | 1 | 1 | 1 |
| (25) | Dispersing Agent | Sodium Metaphosphate | 0.05 | 0.05 | 0.05 |
| (26) | Chelating Agent | Ethylenediaminetetraacetic Acid Trisodium Salt Dihydrate | 0.1 | 0.1 | 0.1 |
| (27) | Antiseptic | Phenoxyethanol | 0.5 | 0.5 | 0.5 |
| (28) | Perfume | Perfume | q.s. | q.s. | q.s. |
|  |  | Total | 100 | 100 | 100 |
| Evaluation | Firm feel |  | C | A | AA |
|  | Lack of stickiness |  | A | A | A |
|  | Emulsion stability |  | A | A | A |

Formulation examples of the oil-in-water emulsion composition for skin of the present disclosure are described below. However, the application examples of the oil-in-water emulsion composition for skin of the present disclosure are not limited by the following formulation examples.

Formulation Example 1 (Table 8)

TABLE 8

|  |  | Formulation Example | 1 |
|---|---|---|---|
| (1) | Water | Ion-exchanged Water | Balance |
| (2) | Moisturizer | Glycerin | 5 |
| (3) |  | 1,3-Butylene Glycol | 10 |
| (4) | Medicant | Tranexamic Acid | 1 |
| (5) |  | Potassium 4-methoxysalicylate | 1 |
| (6) | Thickener | Acrylates/Steareth-20 Methacrylate Copolymer | 0.2 |
| (7) |  | PEG-240/HDI Copolymer Bis-Decyltetradeceth-20 Ether | 0.2 |
| (8) |  | Sodium Acrylate/Sodium Acryloyldimethyl Taurate Copolymer | 0.5 |
| (9) | Neutralizer | Potassium Hydroxide | 0.03 |
| (10) | Surfactant | PEG-40 Stearate | 0.5 |
| (11) |  | Glyceryl Stearate SE | 1 |
| (12) |  | Polysorbate 80 | 0.05 |
| (13) | Oily Component | Stearyl Alcohol | 1 |
| (14) |  | Behenyl Alcohol | 1 |
| (15) |  | Batyl Alcohol | 1 |
| (16) |  | Pentaerythrityl Tetrabehenate/Benzoate/Ethylhexanoate | 2 |
| (17) |  | Petrolatum | 2 |
| (18) |  | Liquid Paraffin | 4 |
| (19) |  | Pentaerythrityl Tetraethylhexanoate | 4 |
| (20) |  | Isododecane | 2 |
| (21) |  | Isohexadecane | 0.1 |
| (22) |  | Polyisobutene (Molecular Weight 55,000) *1 | 0.25 |
| (23) |  | Diphenylsiloxy Phenyl Trimethicone | 10 |
| (24) | Elastomer | Dimethicone/Phenyl Vinyl Dimethicone Crosspolymer | 2 |
| (25) | Powder | Titanium Dioxide | 1 |
| (26) |  | Silica | 1 |
| (27) |  | HDI/Trimethylol Hexyllactone Crosspolymer | 1 |
| (28) | Dispersing Agent | Sodium Metaphosphate | 0.05 |
| (29) | Chelating Agent | Ethylenediaminetetraacetic Acid Trisodium Salt Dihydrate | 0.1 |
| (30) | Antiseptic | Phenoxyethanol | 0.5 |
| (31) | Perfume | Perfume | q.s. |
|  |  | Total | 100 |

Formulation Example 2 (Table 9)

TABLE 9

|  |  | Formulation Example | 2 |
|---|---|---|---|
| (1) | Water | Ion-exchanged Water | Balance |
| (2) | Moisturizer | Glycerin | 8 |
| (3) |  | 1,3-Butylene Glycol | 8 |
| (4) | Medicant | Nicotinamide | 1 |
| (5) |  | Allantoin | 0.05 |
| (6) | Thickener | Acrylates/Steareth-20 Methacrylate Copolymer | 0.2 |
| (7) |  | PEG-240/HDI Copolymer Bis-Decyltetradeceth-20 Ether | 0.2 |
| (8) |  | Ammonium Acryloyldimethyltaurate/Beheneth-25 Methacrylate Crosspolymer | 0.4 |
| (9) | Neutralizer | Potassium Hydroxide | 0.03 |
| (10) | Surfactant | PEG-40 Stearate | 0.5 |
| (11) |  | Glyceryl Stearate SE | 1 |
| (12) | Oily | Stearyl Alcohol | 1 |
| (13) | Component | Behenyl Alcohol | 1 |
| (14) |  | Batyl Alcohol | 1 |
| (15) |  | Pentaerythrityl Tetrabehenate/Benzoate/Ethylhexanoate | 2 |
| (16) |  | Petrolatum | 1.5 |
| (17) |  | Liquid Paraffin | 3 |
| (18) |  | Pentaerythrityl Tetraethylhexanoate | 3 |
| (19) |  | Isododecane | 2 |
| (20) |  | Polyisobutene (Molecular Weight 55,000) *1 | 0.25 |
| (21) |  | Dimethicone | 15 |
| (22) | Elastomer | Polysilicone-11 | 1.5 |
| (23) | Powder | Titanium Dioxide | 1 |
| (24) |  | Silica | 1 |
| (25) |  | HDI/Trimethylol Hexyllactone Crosspolymer | 1 |
| (26) | Dispersing Agent | Sodium Metaphosphate | 0.05 |
| (27) | Chelating Agent | Ethylenediaminetetraacetic Acid Trisodium Salt Dihydrate | 0.1 |
| (28) | Antiseptic | Phenoxyethanol | 0.5 |
| (29) | Perfume | Perfume | q.s. |
|  |  | Total | 100 |

Formulation Example 3 (Table 10)

TABLE 10

|  |  | Formulation Example | 3 |
|---|---|---|---|
| (1) | Water | Ion-exchanged Water | Balance |
| (2) | Moisturizer | Glycerin | 6 |
| (3) |  | 1,3-Butylene Glycol | 7 |
| (4) | Medicant | Retinol | 0.1 |
| (5) | Thickener | Acrylates/Steareth-20 Methacrylate Copolymer | 0.2 |
| (6) |  | PEG-240/HDI Copolymer Bis-Decyltetradeceth-20 Ether | 0.2 |
| (7) |  | Dimethylacrylamide/Sodium Acryloyldimethyltaurate Cross polymer | 0.5 |
| (8) | Neutralizer | Potassium Hydroxide | 0.03 |
| (9) | Surfactant | PEG-40 Stearate | 0.5 |
| (10) |  | Glyceryl Stearate SE | 1 |
| (11) |  | Polysorbate 80 | 0.05 |
| (12) |  | Sorbitan Oleate | 0.02 |
| (13) | Oily | Stearyl Alcohol | 1 |
| (14) | Component | Behenyl Alcohol | 1 |
| (15) |  | Batyl Alcohol | 1 |
| (16) |  | Pentaerythrityl Tetrabehenate/Benzoate/Ethylhexanoate | 1 |
| (17) |  | Petrolatum | 1 |
| (18) |  | Liquid Paraffin | 3 |
| (19) |  | Pentaerythrityl Tetraethylhexanoate | 5 |
| (20) |  | Isododecane | 3 |
| (21) |  | Isohexadecane | 0.1 |
| (22) |  | Polyisobutene (Molecular Weight 55,000) *1 | 0.5 |
| (23) |  | Dimethicone | 8 |
| (24) | Elastomer | Dimethicone/Vinyl Dimethicone Crosspolymer | 2 |
| (25) | Powder | Titanium Dioxide | 1 |
| (26) |  | Silica | 1 |
| (27) |  | HDI/Trimethylol Hexyllactone Crosspolymer | 1 |
| (28) | Dispersing Agent | Sodium Metaphosphate | 0.05 |

TABLE 10-continued

| | | Formulation Example | 3 |
|---|---|---|---|
| (29) | Chelating Agent | Ethylenediaminetetraacetic Acid Trisodium Salt Dihydrate | 0.1 |
| (30) | Antiseptic | Phenoxyethanol | 0.5 |
| (31) | Perfume | Perfume | q.s. |
| | | Total | 100 |

The oil-in-water emulsion composition for skin of the present invention has been described according to the foregoing embodiments and examples, but the invention is not limited to the foregoing embodiments and examples and may encompass various transformations, modifications, and improvements made to the various disclosed elements (including elements disclosed in the Claims, Description, and Drawings) within the scope of the invention and according to the fundamental technical idea of the present invention. Further, various combinations, substitutions, and selections of the various disclosed elements are possible within the scope of the claims of the invention.

Further issues, objectives, and embodiments (including modifications) of the present invention are revealed also from the entire disclosure of the invention including the Claims.

The numerical ranges disclosed herein are to be construed in such a manner that arbitrary numerical values and ranges falling within the disclosed ranges are treated as being concretely described herein, even where not specifically stated.

The invention claimed is:

1. An oil-in-water emulsion composition, for skin that is applied to the skin except for a lip, comprising:
   0.2 to 2.5% by mass of polyisobutene having a relative mass in a range of 30,000 to 100,000;
   0.1 to 3% by mass of a thickener; and
   0.1 to 6% by mass of an elastomer;
   wherein the thickener includes at least one of a homopolymer, a copolymer including a 2-acrylamido-2-methylpropanesulfonic acid component, and a salt of either one thereof; and
   wherein the elastomer is a crosslinked organopolysiloxane comprising silicone polymer crosslinked in three dimensions, the crosslinked organopolysiloxane comprising at least one selected from the group consisting of dimethicone crosspolymer, dimethicone/vinyl dimethicone crosspolymer, dimethicone/phenyl vinyl dimethicone crosspolymer, vinyl dimethicone/lauryl dimethicone crosspolymer, lauryl polydimethyl siloxyethyl dimethicone/bis-vinyl dimethicone crosspolymer, alkyl ($C_{30-45}$) cetearyl dimethicone crosspolymer, polysilicone-11, and cetearyl dimethicone crosspolymer.

2. The composition according to claim 1, wherein:
the crosslinked organopolysiloxane comprises at least one selected from the group consisting of dimethicone crosspolymer, dimethicone/vinyl dimethicone crosspolymer, dimethicone/phenyl vinyl dimethicone crosspolymer, and polysilicone-11.

3. The composition according to claim 1, wherein:
the thickener comprises an electrostatic-repulsive thickener and/or an associative thickener.

4. The composition according to claim 3, wherein:
the electrostatic-repulsive thickener comprises a taurate-based synthetic polymer and/or acrylate-based synthetic polymer.

5. The composition according to claim 2, wherein:
the thickener comprises an electrostatic-repulsive thickener and/or an associative thickener.

6. The composition according to claim 5, wherein:
the electrostatic-repulsive thickener comprises a taurate-based synthetic polymer and/or acrylate-based synthetic polymer.

7. The composition according to claim 1, wherein:
the thickener comprises at least one selected from the group consisting of an ammonium acryloyldimethyltaurate/beheneth-25 methacrylate crosspolymer, ammonium acryloyldimethyltaurate/vinylpyrrolidone copolymer, ammonium acryloyldimethyltaurate/carboxyethyl acrylate crosspolymer, polyacrylate crosspolymer-11, dimethylacrylamide/sodium acryloyldimethyltaurate crosspolymer, hydroxyethyl acrylate/sodium acryloyldimethyltaurate copolymer, sodium acrylate/acryloyldimethyl taurine/dimethylacrylamide crosspolymer, sodium acryloyldimethyltaurate/methacrylamidolauric acid copolymer, acrylamide/sodium acryloyldimethyltaurate/acrylic acid copolymer, acrylate/steareth-20 methacrylate copolymer, and PEG-240/decyltetradeceth-20/hexamethyldiisocyanate copolymer.

8. The composition according to claim 2, wherein:
the thickener comprises at least one selected from the group consisting of an ammonium acryloyldimethyltaurate/beheneth-25 methacrylate crosspolymer, ammonium acryloyldimethyltaurate/vinylpyrrolidone copolymer, ammonium acryloyldimethyltaurate/carboxyethyl acrylate crosspolymer, polyacrylate crosspolymer-11, dimethylacrylamide/sodium acryloyldimethyltaurate crosspolymer, hydroxyethyl acrylate/sodium acryloyldimethyltaurate copolymer, sodium acrylate/acryloyldimethyl taurine/dimethylacrylamide crosspolymer, sodium acryloyldimethyltaurate/methacrylamidolauric acid copolymer, acrylamide/sodium acryloyldimethyltaurate/acrylic acid copolymer, acrylate/steareth-20 methacrylate copolymer, and PEG-240/decyltetradeceth-20/hexamethyldiisocyanate copolymer.

9. The composition according to claim 1, further comprising:
0.5 to 10% by mass of a hydrocarbon oil in which the polyisobutene is soluble.

10. The composition according to claim 9, wherein:
the hydrocarbon oil is volatile.

11. The composition according to claim 2, further comprising:
0.5 to 10% by mass of a hydrocarbon oil in which the polyisobutene is soluble.

12. The composition according to claim 11, wherein:
the hydrocarbon oil is volatile.

13. The composition according to claim 7, further comprising:
- 0.5 to 10% by mass of a hydrocarbon oil in which the polyisobutene is soluble.

14. The composition according to claim 13, wherein: the hydrocarbon oil is volatile.

15. The composition according to claim 1, further comprising:
- a pigment, the amount of the pigment being at most 4% by mass of the composition.

16. The composition according to claim 1, wherein: the composition is to be applied with the hand.

17. The composition according to claim 1, wherein: the composition is to be applied around an eye.

18. The composition according to claim 1, wherein: the composition is for providing a firm sensation to the skin.

19. The composition according to claim 1, wherein: the elastomer content is 0.2 to 5% by mass.

* * * * *